US00PP17093P2

(12) United States Plant Patent
Hansen et al.

(10) Patent No.: US PP17,093 P2
(45) Date of Patent: Sep. 12, 2006

(54) ***HOSTA* PLANT NAMED 'ATLANTIS'**

(50) Latin Name: ***Hosta* sp.**
Varietal Denomination: Atlantis

(76) Inventors: Hans Andrew Hansen, 15605 Snake Trail, Waseca, MN (US) 56093; Tony Avent, 9241 Saul's Rd., Raleigh, NC (US) 27603

( * ) Notice: Subject to any disclaimer, the term of this patent is extended or adjusted under 35 U.S.C. 154(b) by 22 days.

(21) Appl. No.: 11/099,754

(22) Filed: Apr. 6, 2005

(51) Int. Cl.
*A01H 5/00* (2006.01)

(52) U.S. Cl. ..... Plt./353
(58) Field of Classification Search ..... Plt./353
See application file for complete search history.

(56) References Cited

PUBLICATIONS

Garden Web Glossary of Botanical Terms [online], [retrieved on Dec. 19, 2005]. Retrieved from the Internet <http://glossary.gardenweb.com/glossary/nph–ind.cgi?scrug=16677&k=sport&b=and&r=root&s=both> one page only.*

* cited by examiner

*Primary Examiner*—Kent Bell
*Assistant Examiner*—June Hwu
(74) *Attorney, Agent, or Firm*—Penny J. Aguirre

(57) ABSTRACT

A new cultivar of *Hosta* named 'Atlantis', a sport of *Hosta* 'Abba Dabba Do', that is characterized by its unique variegated foliage with green centers and wide yellow-green margins comprising about on third of the leaf area. 'Atlantis' is a large *Hosta* with an upright, mounded habit, a vigorous growth rate, and lavender flowers held on upright scapes in mid summer.

2 Drawing Sheets

Botanical classification: *Hosta* sp.
Cultivar designation: 'Atlantis'.

BACKGROUND OF THE INVENTION

The present invention, *Hosta* 'Atlantis', relates to a new and distinct cultivar of *Hosta,* botanically known as a *Hosta* hybrid, hereinafter referred to as 'Atlantis'.

The inventors discovered the new cultivar, 'Atlantis', in summer of 1998 in a cultivated growing area in Waseca, Minn. 'Atlantis' originated as a naturally occurring chimeral mutation of *Hosta* 'Abba Dabba Do' (unpatented). The parent plant, *Hosta,* 'Abba Dabba Do', is a variegated mutation of the gold foliaged cultivar, *Hosta* 'Sun Power' (unpatented). 'Atlantis' is unique in having wide yellow-green margins surrounding green centers. The variegation pattern is similar to the parent plant 'Abba Dabba Do', however the margins of 'Atlantis' are significantly wider. 'Atlantis' has a similar leaf variegation pattern to 'Satisfaction' (unpatented) and *H. montana* 'Aureo Marginata'. In comparison to 'Atlantis', the leaves of 'Satisfaction' are broader, more heart-shaped, and lack the terminal twist at the leaf apex. 'Aureo Marginata' differs from 'Atlantis' in having a more mounded, less upright plant habit, leaf blades that curve more downward and leaf blades that lack the twist at the apex.

Asexual reproduction of the new cultivar was first accomplished by the inventors utilizing *in vitro* propagation in Waseca, Minn. in fall of 2002. Asexual reproduction of the new cultivar by division and tissue culture has shown that the unique features of 'Atlantis' are stable and reproduced true to type in successive generations.

SUMMARY OF THE INVENTION

The following traits have been repeatedly observed in trials in North Carolina and Minnesota for a period of six years and represent the characteristics of the new cultivar. These attributes in combination distinguish 'Atlantis' as a new and unique cultivar of *Hosta.*

1. The foliage of 'Atlantis' is variegated with yellow-green margins and green centers. The margins of 'Atlantis' comprise about one third of the leaf area, the margins are much wider than the parent plant, 'Abba Dabba Do'.
2. The plant habit of 'Atlantis' is upright and mounding.
3. 'Atlantis' reaches a height of about 77 cm, exclusive of flower scapes, and a spread of about 178 cm in six years.
4. 'Atlantis' has large leaves with undulating margins with a twist at the leaf apex.
5. 'Atlantis' blooms in mid summer with pale lavender flowers that arise above the foliage.

BRIEF DESCRIPTION OF THE DRAWING

The accompanying colored photographs illustrate the overall appearance and distinct characteristics of the new *Hosta.* The photographs were taken of mature plants of 'Atlantis' and 'Abba Dabba Do' as grown outdoor in Waseca, Minn. under the same conditions for six years.

Figure 1:
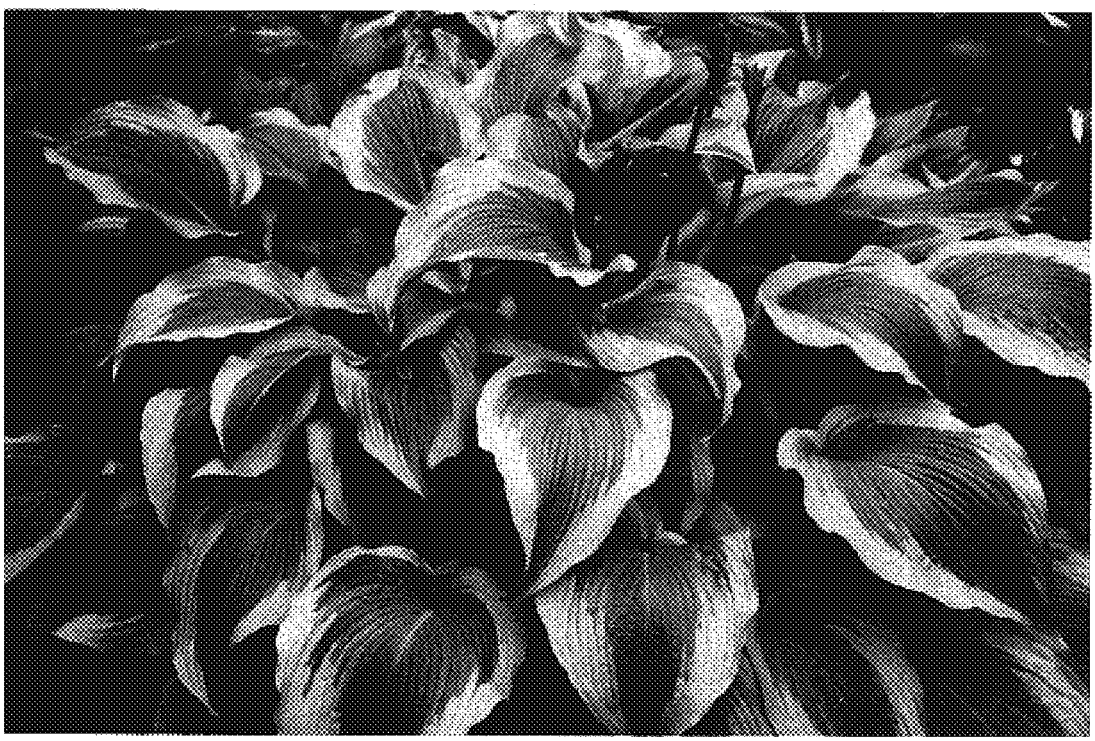
FIG. 1 was taken in June and provides an overall view of the foliage and plant habit of the new cultivar, 'Atlantis'.
Figure 2:
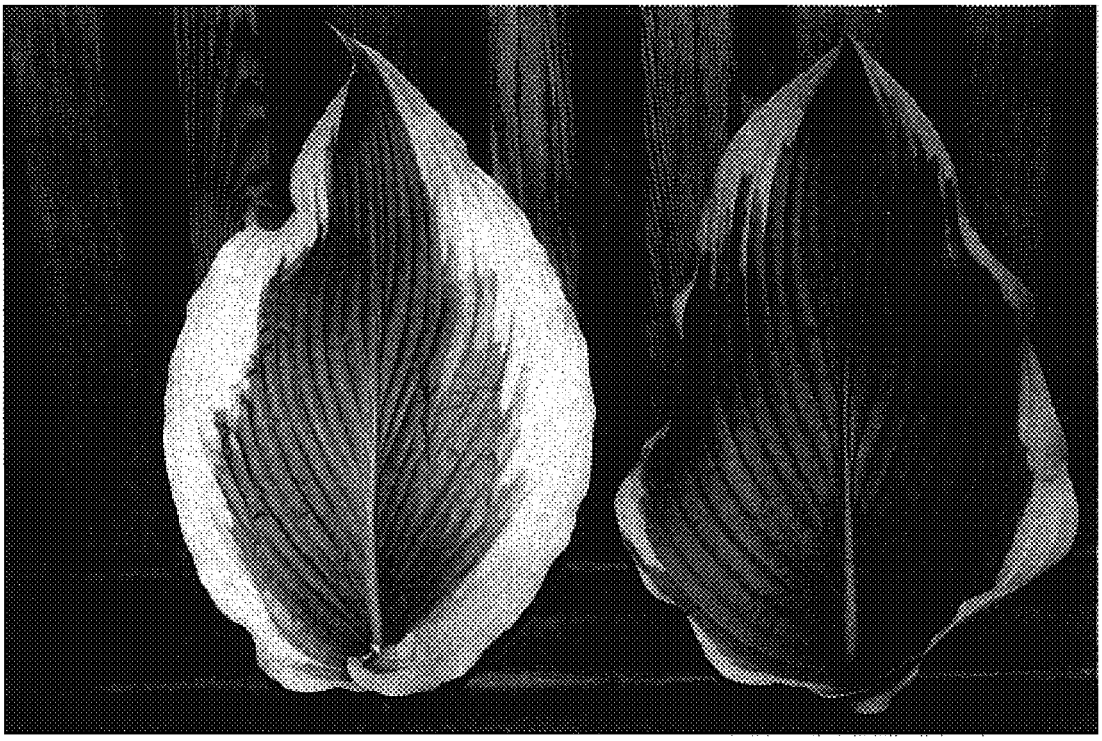

The photograph in FIG. 2 was taken in August and provides a comparison between a leaf of 'Atlantis' (shown on left) and 'Abba Dabba Do' (shown on right) as grown in light shade.

The colors in the photographs are as close as possible with the photographic and printing technology utilized and combined with the color values cited in the detailed botanical description accurately describe the colors of the new *Hosta.*

DETAILED BOTANICAL DESCRIPTION OF THE PLANT

The following is a detailed description of 6 year-old plants of the new cultivar as grown outdoors in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Atlantis' is a cultivar of *Hosta* of hybrid origin.

Parentage: Naturally occurring chimeral mutation of *Hosta* 'Abba Dabba Do' (not patented).

General description:

*Blooming period.*—About 3 to 4 weeks from early July to early August.

*Plant habit.*—Herbaceous perennial, clump-forming, upright and mounded foliage of large size.

*Height and spread.*—Reaches about 77 cm in height (excluding flower scapes) and about 178 cm in width.

*Hardiness.*—Zone 3–8.

*Culture.*—Light shade to medium shade, moist soils of moderate fertility. Margin color is lighter in deeper shade.

*Diseases and pests.*—No susceptibility or resistance to diseases or pests has been observed for 'Atlantis'.

*Root description.*—Freely branched, fleshy.

*Propagation.*—*In vitro* propagation is the preferred method utilizing typical methods for *Hosta,* division is also possible.

*Root development.*—Rooted transplants from tissue culture fully develop in a 96-cell liner in about 6 to 8 weeks in a greenhouse with average temperatures of about 70° F.

*Growth rate.*—Vigorous.

Foliage description:

*Leaf shape.*—Broadly ovate.

*Leaf division.*—Simple.

*Leaf base.*—Cordate.

*Leaf apex.*—Cuspidate, typically with a twist at the tip when leaves are mature.

*Leaf venation.*—16 to 18 pairs of veins, camptodrome pattern, impressed on upper surface and raised on lower surface, color matches leaf coloration.

*Leaf margins.*—Entire, slightly wavy.

*Leaf attachment.*—Petiolate.

*Leaf arrangement.*—Basal, radiate spirally from base.

*Leaf surface.*—Upper glabrous, lower glaucous.

*Leaf substance.*—Average.

*Leaf orientation.*—Held horizontal on upright petioles.

*Leaf color.*—Spring foliage (upper and lower surface); centers 137A, margins 144B, irregular intermediate area between the margins and centers 146C. Mature leaves (upper and lower surface); centers 137A, margins 144B when grown in heavy shade and 8C when grown in light shade, intermediate area 146C.

*Leaf variegation pattern.*—Margins about 2.5 to 6 cm in width, comprising about one third of the leaf area.

*Leaf size.*—About 32 cm in length, about 20 cm in width.

*Leaf quantity.*—About 5 to 7 per shoot (eye).

*Petiole size.*—About 48 to 54 cm in length, about 1.5 to 1.75 cm in width.

*Petiole color.*—Inner surface 138B, outer surface 138C.

*Petiole surface.*—Glabrous.

*Petiole shape.*—Sulcate.

Flower scape description:

*Scape shape.*—Round, solid.

*Scape number.*—One per mature eye under normal growing conditions.

*Scape posture.*—Straight, held upright at about 80 to 90° from horizontal.

*Scape size.*—About 115 cm in length, about 1 cm in width.

*Scape color.*—137A.

*Scape surface.*—Glabrous.

*Leaf bracts.*—1 per scape if present, centers are 137A in color, margins are 144B in color, ovate in shape, average of 2.5 cm in length and 1.2 cm in width, occur 43 cm from base of plant.

Flower description:

*Inflorescence type.*—Terminal racemes of bell-shaped flowers on elongated scapes.

*Lastingness of inflorescence.*—About 3 to 4 weeks from first opening bloom to fading of last opening bloom, individual blooms last about one day.

*Flower shape.*—Bell-shaped.

*Flower number.*—32 to 45 per scape.

*Flower internode length.*—About 4 cm.

*Flower fragrance.*—None detected.

*Flower bud shape.*—Spathulate.

*Flower bud size.*—About 4.5 cm in length and 1.5 cm in diameter.

*Flower bud color.*—Emerges 85C with markings of 85D, matures to 85D with markings of 85C.

*Flower size.*—About 5 cm in length and about 4 cm in diameter including tube portion, tube portion is 2 cm in length and 4 mm in diameter.

*Flower color.*—91D (violet-blue).

*Pedicels.*—About 1.5 cm in length, 2 mm in diameter, 91D in color, glabrous surface.

*Perianth features.*—Comprised of 6 tepals, 3 interior and 3 exterior, overlapping in expanded region and fused in tube region.

*Tepal shape.*—Oblanceolate.

*Tepal size.*—About 4 cm in length, up to 1.5 cm in width.

*Tepal color.*—Outer surface 91D, inner surface 91D with center markings about 5 mm in width of 85A.

*Tepal texture.*—Glabrous.

*Tepal margin.*—Entire.

*Tepal apex.*—Acute.

*Floral bracts.*—1 per flower, ovate in shape, glabrous surface, 146D in color, up to 4 cm in length and 2 cm in width (larger at base of plant decreasing in size towards apex), clasping base, acute apex.

Reproductive organs:

*Gynoecium.*—1 Pistil, extends about 1 cm beyond apex of tepals, 5 to 6 cm in length, 8D in color, stigma is 3-lobed and 8D in color, ovary is superior, compound, composed of 3 locules, 8 mm in length, 3 mm in width, 145C in color.

*Androcoecium.*—6 stamens, 8D in color, 5 cm in length, 1 mm in width, distal portion is curved, length is equal or slightly shorter than edge of tepals, anthers are 3 mm in length, 1 mm in width, attachment is versatile, 202A in color, dehiscence is longitudinal, pollen is abundant and 15B in color.

*Fruit.*—Capsule, 3-chambered, about 2.5 to 3 cm in length, 8 mm in width, 137A, in color.

*Seeds.*—25 to 30 seeds per capsule, about 5 to 6 mm in length and 3 mm in width, 202A in color.

We claim:

1. A new and distinct cultivar of *Hosta* plant named 'Atlantis' as herein illustrated and described.

* * * * *